United States Patent
Kaneko et al.

(10) Patent No.: US 8,552,407 B2
(45) Date of Patent: Oct. 8, 2013

(54) ION MILLING DEVICE

(75) Inventors: Asako Kaneko, Hitachinaka (JP); Hirobumi Muto, Hitachinaka (JP); Atsushi Kamino, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/386,980

(22) PCT Filed: Jul. 14, 2010

(86) PCT No.: PCT/JP2010/004555
§ 371 (c)(1),
(2), (4) Date: Jan. 25, 2012

(87) PCT Pub. No.: WO2011/013311
PCT Pub. Date: Feb. 3, 2011

(65) Prior Publication Data
US 2012/0126146 A1 May 24, 2012

(30) Foreign Application Priority Data
Jul. 30, 2009 (JP) ................................. 2009-177184

(51) Int. Cl.
*G01N 1/32* (2006.01)
(52) U.S. Cl.
USPC .................... 250/492.3; 250/492.1; 250/505.1
(58) Field of Classification Search
None
See application file for complete search history.

(56) References Cited

U.S. PATENT DOCUMENTS

| 4,512,848 | A | * | 4/1985 | Deckman et al. | 216/43 |
|---|---|---|---|---|---|
| 5,852,298 | A | * | 12/1998 | Hatakeyama et al. | 250/492.2 |
| 6,038,106 | A | * | 3/2000 | Aboaf et al. | 360/317 |
| 6,618,174 | B2 | * | 9/2003 | Parker et al. | 359/15 |
| 6,965,138 | B2 | * | 11/2005 | Nakajima et al. | 257/295 |
| 7,099,057 | B2 | * | 8/2006 | Parker et al. | 359/15 |
| 7,291,506 | B2 | * | 11/2007 | Nakajima et al. | 438/3 |
| 7,993,535 | B2 | * | 8/2011 | Jiang et al. | 216/17 |
| 2002/0039209 | A1 | * | 4/2002 | Parker et al. | 359/15 |
| 2004/0047014 | A1 | * | 3/2004 | Parker et al. | 359/15 |
| 2004/0051213 | A1 | * | 3/2004 | Muratoglu | 264/494 |
| 2005/0020011 | A1 | * | 1/2005 | Nakajima et al. | 438/257 |
| 2005/0058913 | A1 | * | 3/2005 | Osada et al. | 430/5 |
| 2005/0081997 | A1 | * | 4/2005 | Yoshioka et al. | 156/345.3 |
| 2005/0254289 | A1 | * | 11/2005 | Nakajima et al. | 365/158 |
| 2006/0291024 | A1 | * | 12/2006 | Parker et al. | 359/15 |
| 2008/0067443 | A1 | * | 3/2008 | Todoroki et al. | 250/492.21 |
| 2008/0262120 | A1 | * | 10/2008 | Muratoglu | 522/81 |
| 2010/0003768 | A1 | * | 1/2010 | Barnes et al. | 438/4 |

FOREIGN PATENT DOCUMENTS

JP 2003-173754 A 6/2003
JP 2005-37164 A 2/2005
(Continued)

*Primary Examiner* — Andrew Smyth
(74) *Attorney, Agent, or Firm* — Mattingly & Malur, PC

(57) ABSTRACT

Disclosed is a shield (8, 10) disposed between an ion source (1) of an ion milling device and a sample (7) so as to be in contact with the sample. The shield is characterized by having a circular shape having an opening at the center, and by being capable of rotating about an axis (11) extending through the opening. Further, a groove is provided in the ion source-side surface of an end portion of the shield, and an inclined surface is provided on an end portion of the shield. Thus, an ion milling device having a shield, wherein the maximum number of machining operations can be increased, and the position of the shield can be accurately adjusted.

7 Claims, 4 Drawing Sheets

(56) References Cited

FOREIGN PATENT DOCUMENTS

| | | | | |
|---|---|---|---|---|
| JP | 2005037164 | A | * | 2/2005 |
| JP | 2005-062131 | A | | 3/2005 |
| JP | 2006-269342 | A | | 10/2006 |
| JP | 2008-039667 | A | | 2/2008 |
| JP | 2008039667 | A | * | 2/2008 |
| JP | 2009-097934 | A | | 5/2009 |
| JP | 2009097934 | A | * | 5/2009 |

* cited by examiner (a)

(b)

ION MILLING DEVICE

TECHNICAL FIELD

The present invention relates to a shield for ion milling devices, by which a sample for an electron scanning microscope or the like is fabricated.

BACKGROUND ART

Ion milling devices are ones which may be used for scraping a sample by means of a sputtering phenomenon. Ion beams, which are arranged properly in energy and direction, are accelerated and irradiated on the sample to spring out sample atoms from a surface of the sample.

At the time of working a sample, a shield (referred to below as a mask) for ion beams is put on an upper surface of the sample except in a working target position in order to prevent the scattering of ion beams from damaging the sample except in the working target position. The sample is thus made to project from the shield. A projected sample portion is subjected to sputtering whereby a sample section can be worked to be made smooth.

The technology in patent documents 1 and 2 is conventionally known for ion milling devices.

CITATION LIST

Patent Literature

Patent Literature 1: JP-A-2005-62131
Patent Literature 2: JP-A-2006-269342

SUMMARY OF THE INVENTION

Technical Problem

Masks for conventional ion milling devices are typically polygonal-shaped such as square-shaped or rectangular-shaped. However, the following problems are involved in conventional, polygonal-shaped masks.

First, polygonal-shaped masks involve a problem that in order to maintain a surface in contact with a sample flat, a high processing technique is required for manufacturers and a high cost is involved. In addition, since a mask is consumed due to the sputtering phenomenon, the possible number of times of working every mask is small in terms of configuration with polygonal-shaped masks. It is necessary to remount a mask on a fixation plate a plurality of times in using four sides of a single mask.

Secondly, a mask is positionally regulated by means of an optical microscope in order to accurately regulate the position of the mask and a shielded position of a sample. In this method of positional regulation, when illumination is caused to strike perpendicularly to the sample, illuminating light strikes on the mask and the sample. An associated regulator observes the mask and the sample but contrast in a field of view is decreased due to mirror reflection to make it difficult to distinguish a boundary between the two.

Thirdly, in the case where a mask end surface is perpendicular to a sample surface in regulating a shielded position, a side of the mask in contact with the sample surface and a side of the mask not in contact with the sample surface agree with each other when observed from above the sample and the mask with the use of an optical microscope. At this time, since the optical microscope is small in depth of focus, it is difficult to focus on both an upper surface of the mask and on the sample, so that it is difficult to exactly regulate an amount of projection of the sample from the mask end surface.

In view of such problems, an object of the present invention is to provide an ion milling device having a shield which is capable of increasing the possible number of times of working and for accurately regulating a shield position.

Solution to Problem

In order to solve the first problem, the present invention provides a shield which is used for an ion milling device, by which ion beams emitted from an ion source are irradiated on a sample to work the sample, and in which the shield is arranged in a position between the sample and the ion source and in contact with the sample. The shield is circular and is configured to have an opening centrally thereof. The shield is capable of rotating about an axis extending through the opening.

By making a shield circular in shape, it is possible to fabricate a shield for ion milling, which does not require a high processing technique and which is low in cost. Also, owing to the rotation of the shield about a center of a shield, the possible number of times of working per one mask can be increased in a one time mask mounting.

In order to solve the second problem, a groove is provided on a surface of an end of the shield on a side toward the ion source. Thereby, mirror reflection from the shield can be decreased, thus achieving an improvement in contrast to make it easy to distinguish a boundary between a sample and the shield.

In order to solve the third problem, an inclined surface is provided on an end of the shield and the shield is shaped into a truncated cone, which enlarges as the shield toward a surface of the sample. Thereby, a side of the shield which is in contact with a sample surface and a side of the shield which is not in contact with the sample surface are not in agreement with each other and it is made easy to focus on a sample and a side of the shield in contact with the sample.

Advantageous Effects of the Invention

According to the present invention, it is possible to provide a shield for ion milling and an ion milling device, which do not require a high processing technique and are low in cost. Also, it is possible to provide a shield for ion milling and an ion milling device capable of accurately regulating a shield position.

BRIEF DESCRIPTION OF DRAWINGS

An embodiment of an ion milling device and a shield (mask) in accordance with the present invention will be described hereinafter with reference to the drawings.

DESCRIPTION OF PREFERRED EMBODIMENT

Figure 1:
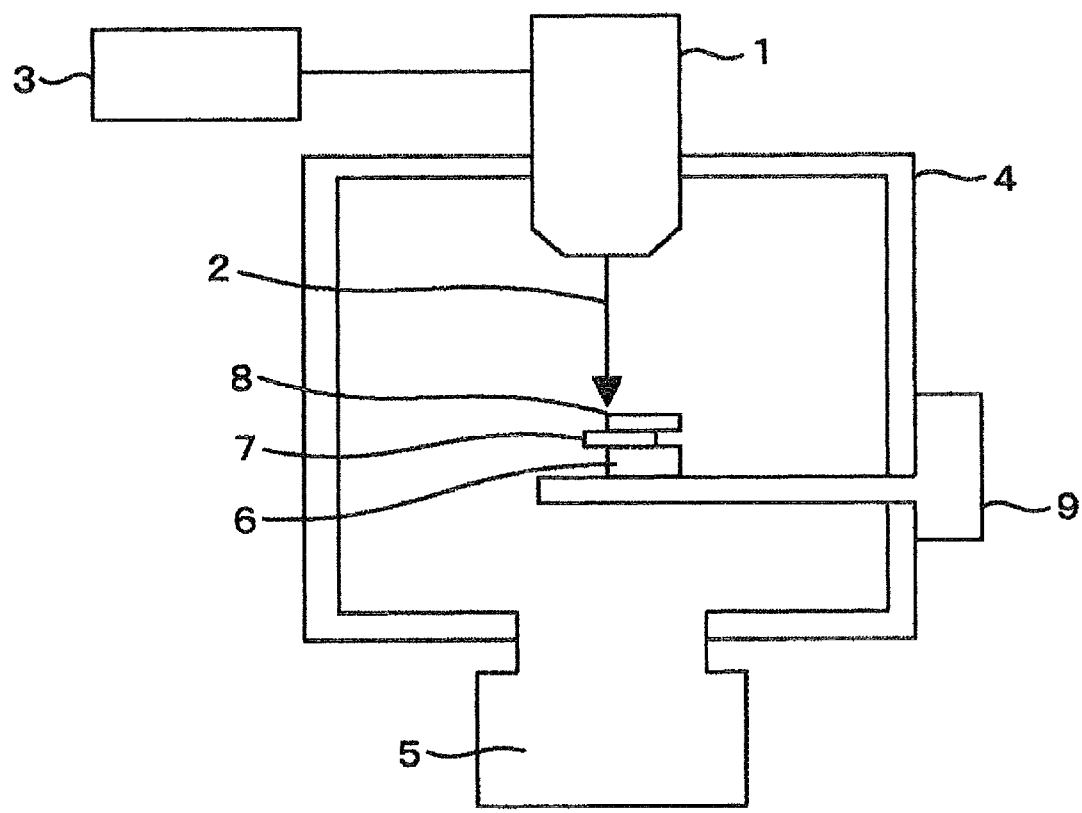
FIG. 1 is a schematic view showing an ion milling device.

FIG. 1 shows the construction of an ion milling device, in which a mask 8 is mounted on an upper surface of a sample 7.

Ion beams 2, as accelerated, are irradiated, and a sputtering phenomenon of the ions is made use of to work on the section of a projecting portion of the sample. For example, argon ion beams can be used as the ion beams 2.

A current density of argon ions in an ion source 1 is controlled by an ion source control unit 3. It is possible to control a vacuum evacuation system 5 to put the interior of a vacuum chamber 4 in a vacuum or sub-atmospheric state and to maintain the state. The sample 7 is fixed on a sample support 6. Also, when the interior of the vacuum chamber 4 is opened to the atmosphere, a sample stage 9 can be drawn outside the vacuum chamber 4. The sample support 6, with the sample 7 fixed thereto, can be fixed onto the sample stage 9.

By fixing the mask 8 onto the sample 7 and irradiating the ion beams 2 discharged from the ion source 1, it is possible to work a portion of the sample 7 projected from the mask 8.

Figure 2:
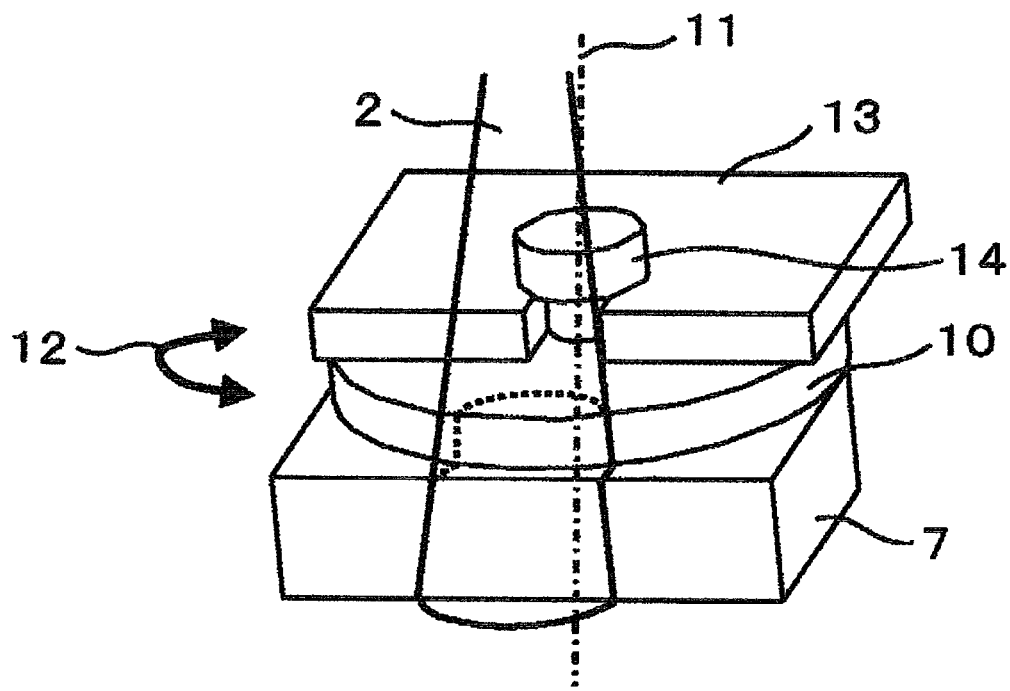
FIG. 2(a) and FIG. 2(b)) show views illustrating a state, in which a shield, according to an embodiment of the present invention, which is fixed to a shield fixation plate, is mounted on an upper surface of a sample and ion beams are irradiated thereon.
Figure 2:
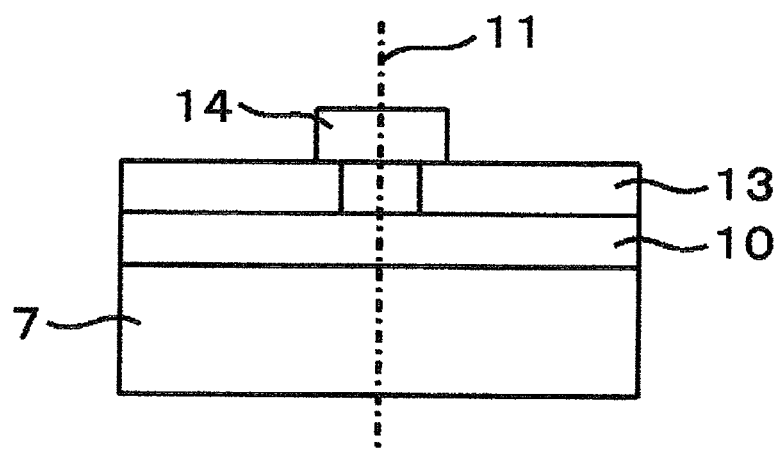

FIG. 2(a) and FIG. 2(b)) show views illustrating the mask 8 according to the present invention.

FIG. 2(a) shows a state, in which a circular mask 10, which is fixed to a mask fixation plate 13, is mounted on an upper surface of the sample 7 and the ion beams 2 are irradiated on the circular mask 10 and the sample 7. Thus it is possible to irradiate the ion beams 2 to work a target position of the sample 7. While a worked surface of the sample is somewhat rounded, a region observed by an electron microscope is fairly small and there is no problem in observation.

FIG. 2(b) is a side view showing the circular mask 10. The circular mask 10 is formed, at a center thereof, with an opening to enable rotating it about an axis, depicted here as a screw 14 defining the axis, and passing through the opening in the circular mask 14. After working, the screw 14 is loosened and a worked surface of the circular mask 10 is moved in a mask rotating direction 12 shown in FIG. 2(a) with a mask center 11 as an axis. It is possible to freely the set a rotation amount and it suffices to put an undamaged portion of mask 10 in a position of ion irradiation. Thereby, mounting the circular mask 10 once makes it possible to increase the possible number of times of working per one mask.

Figure 3:
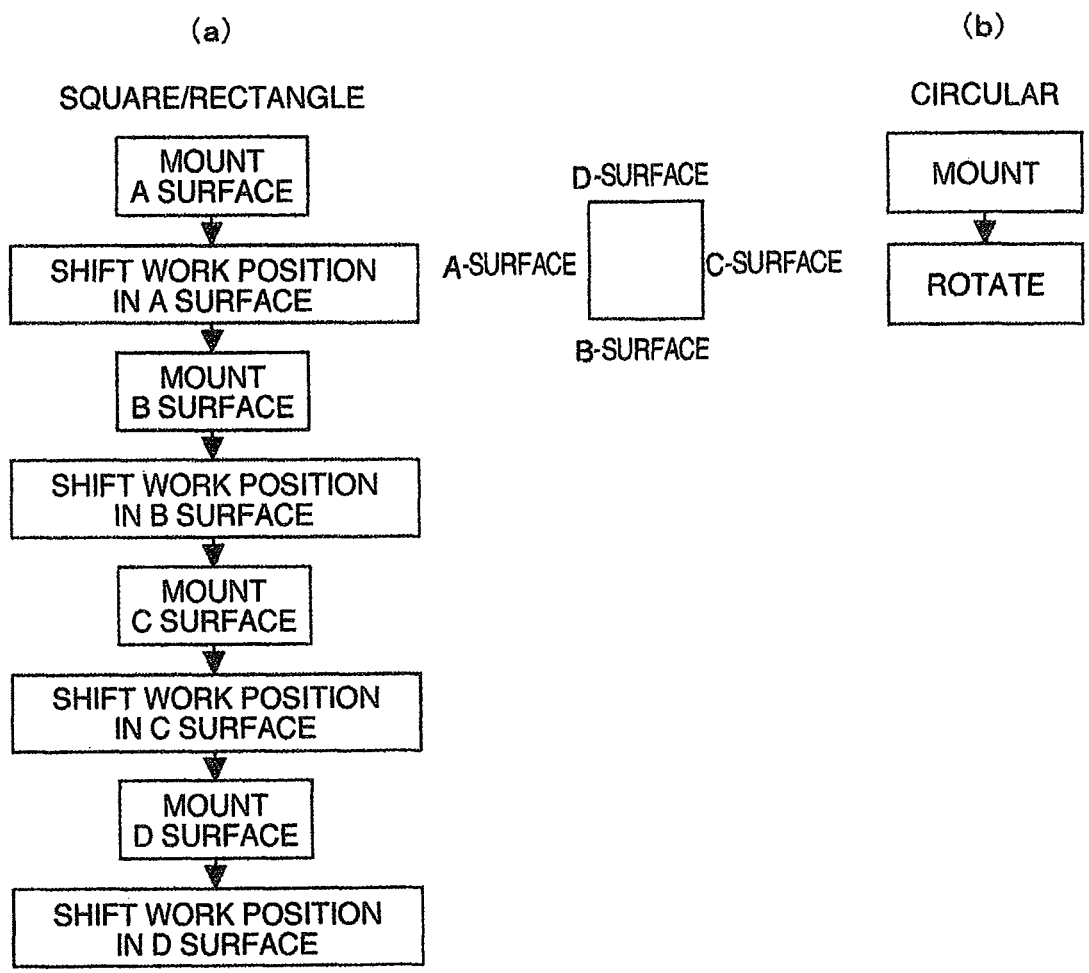
FIG. 3(a) and FIG. 3(b)) show flowcharts showing processes of mounting a shield.

FIG. 3(a) and FIG. 3(b)) show processes of mounting a mask, FIG. 3(a) showing the process of mounting a conventional, square mask, and FIG. 3(b) showing the process of mounting a circular mask in accordance with the present invention. With the conventional mask, it is necessary to remount the mask on a mask fixation plate four times in using all the end surfaces of the mask. On the other hand, with the mask in accordance with the present invention, it is possible to use the whole end surface of the mask when the mask is mounted only once on the mask fixation plate. It suffices to loosen the screw 14, which fixes the mask 10 and the mask fixation plate 13 together, to rotate the mask 10. It is possible to freely set the rotation amount and it suffices to put an undamaged portion of mask 10 in a position of ion irradiation.

Figure 4:
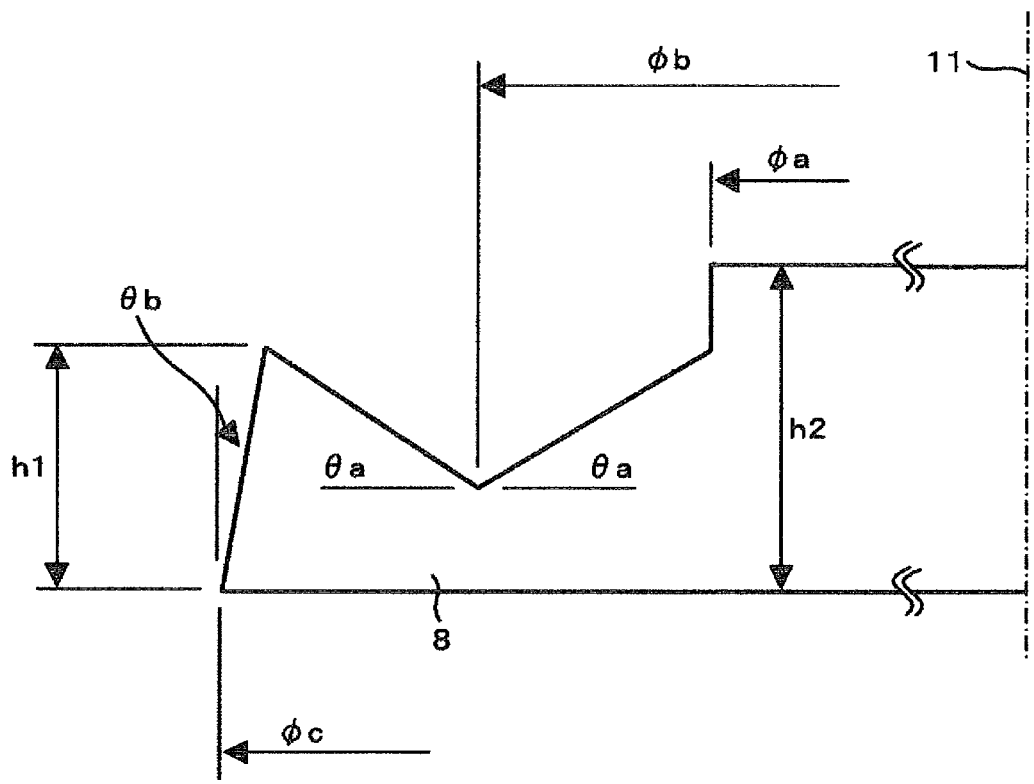
FIG. 4 is a cross-sectional view showing the neighborhood of an end surface of the shield according to an embodiment of the invention.

FIG. 4 is a view showing a sectional structure of the mask in the invention. First, a mask groove, having a mask groove slope θa, is formed in the mask about groove axis pb. Owing to the groove, in positioning the mask by the use of an optical microscope, light emitted from a lighting luminous source of the optical microscope can be suppressed from being reflected on the sample to be incident on an objective lens. Thereby, a field of view is increased in contrast to enable facilitating positioning of the mask.

Also, an inclined mask end surface of θb is formed. The inclined mask end surface θb is formed so that the mask is shaped into a truncated cone having a peak and, which truncated cone enlarges as it goes toward the surface of the sample. Thereby, in positioning the mask by the use of the optical microscope, it is made easy to focus the optical microscope on a boundary between a tip end of the mask and the sample, so that positioning of the mask is facilitated.

In addition, it is possible to optionally select the mask groove slope θa for varying the shape of the groove. Also, both of the sides of the mask groove are not necessarily the same groove slope θa. Also, for the inclined mask end surface, it is possible to optionally select an angle θb.

While the groove θa and the inclination θb of the inclined mask end surface shown in FIG. 4 are not necessarily limited to a circular mask, the circular mask can facilitate working of such groove and such inclination.

In addition, the optical microscope is mounted so as to have its field of view positioned in a position, in which the end of the shield or the mask 10 and the sample 7 are disposed. Since it is general that the optical microscope is not used when the sample 7 is worked, it is prepared separately from the ion milling device and selectively used at the time of positioning of the mask 10 and the sample 7. When positioning is performed with the optical microscope, the sample 7, the mask 10 and the mask fixation plate 13 are placed in this order on a sample holder 6 having been taken out of the ion milling device, a relative position between the sample and the mask is regulated and they are held on the sample holder 6 by means of fixation members such as screws 14, and the like. At this time, with the mask 10 having the above-mentioned end surface θb and the above-mentioned groove, the optical axis of the optical microscope is usually set in parallel to the axis of the mask center 11, so that perpendiculars to the end surface θb and surfaces θa, which define the groove, are not parallel to the optical axis of the optical microscope. Therefore, at the time of positioning of the mask 10, reflected light can be suppressed from being incident on the objective lens of the optical microscope to obstruct the field of view of the optical microscope.

REFERENCE SIGNS LIST 1 ion source
2 ion beams
3 ion source control unit
4 vacuum chamber
5 vacuum evacuation system
6 sample support
7 sample
8 shield (mask)
9 sample stage
10 circular mask
11 mask center
12 mask rotating direction
13 mask fixation plate
14 screw

The invention claimed is:

1. A shield used for an ion milling device, by which ion beams emitted from an ion source are irradiated on a sample to work the sample, the shield being arranged in a position between the sample and the ion source and in contact with the sample so that a target surface portion of the sample is capable of being worked by the on beams while shielding the sample from the ion beams except in the target surface portion; and
   wherein the shield is circular and is configured to have an opening centrally thereof and is rotatable with respect to the sample about an axis extending through the opening.

2. The shield according to claim 1, wherein said shield has a groove provided on a shield surface oriented toward the ion source at an end portion of the shield and located adjacent the target surface portion of the sample.

3. The shield according to claim 1, wherein said shield has an inclined surface provided on an end portion of the shield and said shield is shaped into a truncated cone, which enlarges as it goes toward the target surface portion of the sample.

4. A shield used for an ion milling device, by which ion beams emitted from an ion source are irradiated on a target surface portion of a sample to work the sample, the shield being arranged in a position between the sample and the ion source and in contact with the sample, wherein the shield is circular, is configured to have an opening centrally thereof and is rotatable with respect to the sample about an axis extending through the opening and has a first surface arranged to face to the ion beams and to be oblique with respect to the ion beams, and a second surface arranged to be oblique with respect to the ion beams and to be connected to the first surface to form a peak facing to the ion beams between the first surface and the second surface, the second surface forming a groove facing to the ion source.

5. An ion milling device, by which ion beams emitted from an ion source are irradiated on a sample to work the sample, wherein the ion milling device includes a shield arranged in a position between the sample and the ion source and in contact with the sample so that a target surface portion of the sample is capable of being worked by the ion beams while shielding the sample from the ion beams except in the target surface portion; and wherein the shield is circular and has an opening centrally thereof and is rotatable with respect to the sample about an axis extending through the opening.

6. The ion milling device according to claim 5, wherein the shield has a groove provided on a surface of the shield and facing toward the ion source and at an end portion of the shield.

7. The ion milling device according to claim 5, wherein the shield has an inclined surface provided on an end portion of the shield and the shield is shaped into a truncated cone, which enlarges as it goes toward a surface of the sample.

\* \* \* \* \*